United States Patent
Yi et al.

(10) Patent No.: US 9,408,849 B2
(45) Date of Patent: *Aug. 9, 2016

(54) CRYSTAL ENTECAVIR, CRYSTAL ENTECAVIR FORMULATION AND METHODS FOR THE PREPARATION THEREOF

(71) Applicant: Zhejiang Medicine Co., Ltd. Xinchang Pharmaceutical Factory, Donglu, Xinchang County (CN)

(72) Inventors: Deping Yi, Huancheng Donglu (CN); Zhike Tian, Huancheng Donglu (CN); Weidong Ye, Huancheng Donglu (CN)

(73) Assignee: Zhejiang Medicine Co., Ltd. Xinchang Pharmaceutical Factory, Huancheng Donglu (CN)

( * ) Notice: Subject to any disclaimer, the term of this patent is extended or adjusted under 35 U.S.C. 154(b) by 0 days.

This patent is subject to a terminal disclaimer.

(21) Appl. No.: 14/246,029

(22) Filed: Apr. 4, 2014

(65) Prior Publication Data

US 2014/0220120 A1    Aug. 7, 2014

Related U.S. Application Data

(63) Continuation-in-part of application No. 12/674,879, filed as application No. PCT/CN2008/001523 on Aug. 25, 2008, now abandoned, application No. 14/246,029, which is a continuation-in-part of application No. 12/527,215, filed as application No. PCT/CN2008/000249 on Jan. 31, 2008, now Pat. No. 8,937,076.

(30) Foreign Application Priority Data

Feb. 14, 2007    (CN) .......................... 2007 1 0004988
Aug. 23, 2007    (CN) .......................... 2007 1 0143096

(51) Int. Cl.
*A61K 31/522*    (2006.01)
*A61K 9/20*    (2006.01)
*A61K 9/48*    (2006.01)
*C07D 473/18*    (2006.01)

(52) U.S. Cl.
CPC ............. *A61K 31/522* (2013.01); *A61K 9/2027* (2013.01); *A61K 9/2054* (2013.01); *A61K 9/4866* (2013.01); *C07D 473/18* (2013.01)

(58) Field of Classification Search
None
See application file for complete search history.

(56) References Cited

U.S. PATENT DOCUMENTS

2007/0060599 A1*  3/2007  DiMarco .............. C07D 473/18
                                                          514/263.37

* cited by examiner

*Primary Examiner* — David J Blanchard
*Assistant Examiner* — Daniel F Coughlin
(74) *Attorney, Agent, or Firm* — William D. Hare; McNeely Hare & War, LLP

(57) ABSTRACT

The present invention relates to a pharmaceutical composition for treating hepatitis B virus infection comprising crystalline entecavir as the pharmaceutically active ingredient and one or more pharmaceutically acceptable excipients. The tablet and capsule of the pharmaceutical composition have improved stability compared to that of amorphous entecavir under the conditions of light, high temperature and high humidity.

16 Claims, 2 Drawing Sheets

CRYSTAL ENTECAVIR, CRYSTAL ENTECAVIR FORMULATION AND METHODS FOR THE PREPARATION THEREOF

CROSS-REFERENCE TO RELATED APPLICATIONS

This application is a continuation-in-part of U.S. application Ser. No. 12/674,879 filed on Feb. 23, 2010 as a 371 of PCT/CN08/01523 filed on Aug. 25, 2008, which claims priority to CN200710143096.7, filed on Aug. 23, 2007, and of U.S. application Ser. No. 12/527,215 filed on Mar. 22, 2010 as a 371 of PCT/CN2008/000249 filed on Jan. 31, 2008 and claiming priority to CN200710004988.9, filed on Feb. 14, 2007. The contents of both of which are incorporated herein in their entirety by reference.

FIELD OF THE INVENTION

The present invention relates to a crystal entecavir formulation, and its clinical use in the treatment of hepatitis B virus infection.

BACKGROUND OF THE INVENTION

Chronic hepatitis B virus infection is one of the most severe liver diseases in morbidity and death rate in the worldwide range. At present, pharmaceuticals for treating chronic hepatitis B (CHB) virus infection are classified to interferon α and nucleoside/nucleotide analogue, i.e. Lamivudine and Adefovir. However, these pharmaceuticals can not meet needs for doctors and patients in treating chronic hepatitis B virus infection because of their respective limitation. Entecavir (ETV) is referred to as 2'-cyclopentyl deoxyguanosine (BMS2000475) which belongs to analogues of Guanine nucleotide and is phosphorylated to form an active triple phosphate in vivo. The triple phosphate of entecavir inhibits HBV polymerase by competition with 2'-deoxyguanosine-5'-triphosphate as a nature substrate of HBV polymerase, so as to achieve the purpose of effectively treating chronic hepatitis B virus infection and have strong anti-HBV effects. Entecavir, [1S-(1α,3α,4β)]-2-amino-1,9-dihydro-9-[4-hydroxy-3-hydroxymethyl]-2-methylenecyclopentyl]-6H-purin-6-one, monohydrate, and has the molecular formula of $C_{12}H_{15}N_5O_3 \cdot H_2O$ and the molecular weight of 295.3. Its structural formula is as follows:

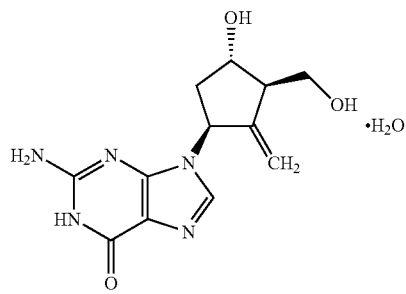

Entecavir was successfully developed by Bristol-Myers Squibb Co. of USA first and the trademark of the product formulation is Baraclude™, including two types of formulations of tablet and oral solution having 0.5 mg and 1 mg of dosage. Chinese publication No. CN1310999 made by COLONNO, Richard, J. et al discloses a low amount of entecavir and uses of the composition containing entecavir in combination with other pharmaceutically active substances for treating hepatitis B virus infection, however, the entecavir is non-crystal. In addition, its oral formulations such as tablet and capsule are made by a boiling granulating process. The process is too complicated to control quality of products during humidity heat treatment even though ensuring uniform distribution of the active ingredients.

The present inventors of the Chinese patent application CN200710004988.9 provides a crystal entecavir in an aqueous solution as active ingredients. It has been found that tablets and capsules produced by a crystal entecavir in an aqueous solution as active ingredients are more stable than that of amorphous entecavir under the conditions of light, high temperature and high humidity.

The object of the present invention is to provide an oral formulation of the composition containing a crystal entecavir and the method of preparing for the same. The method comprises uniformly mixing the active crystal entecavir with glidants (or lubricants), and then uniformly mixing with diluents, adhesives, disintegrants and lubricants, and then directly tabletting or filling capsule. Comparing with processes of wet granulation, boiling granulating or spray drying granulation, the method is simpler in operation, more suitable for industrial production and control of product quantity, reduced energy consumption, and reduced production cost.

SUMMARY OF THE INVENTION

The present invention provides a pharmaceutical composition comprising a crystal entecavir and its use for treatment of hepatitis B virus infection. The composition comprises an amount of from 0.001 mg to 25 mg of a crystal entecavir, preferably an amount of from 0.01 mg to 10 mg of a crystal entecavir, more preferably an amount of from 0.1 mg to 5 mg of a crystal entecavir. The composition is administered for once daily to treat hepatitis B virus infection in an adult human patient upon clinical applications.

The present invention further provides a pharmaceutical composition for oral administrations comprising a crystal entecavir as active ingredients. The active ingredient of the entecavir formulation product for sold is now an amorphous entecavir. However, the crystal entecavir in aqueous solutions used as active ingredients of the present invention has been filed by the present inventors (Chinese patent application No. 200710004988.9), the contents of which is incorporated herein in its entirety by reference.

The present invention further provides a pharmaceutical composition comprising the crystal entecavir, which can be formulated for administration by any suitable means. For example, compositions for oral administration, which are preferred, but not limited, can be in the form of tablets, capsules, granules or powders, in which the tablets and capsules is most preferred.

According to a first aspect of the invention, the present invention further provides a method of preparing for a pharmaceutical composition comprising the crystal entecavir in the form of tablets and capsules, but not directly limited process of tabletting or filling, wet granulation, boiling granulating or spray drying granulation, and process of directly tabletting or filling is preferred. The process of directly tabletting or filling comprises uniformly mixing the active crystal entecavir with glidants (or lubricants), then uniformly mixing with diluents, adhesives, and disintegrants, and then directly tabletting or filling capsule. Compared to the processes of wet granulation, boiling granulating or spray drying granulation, the present method is simpler in operation, more suitable for industrialized production and control of product quantity, reduced energy consumption, and reduced production costs.

The technical solution is as follows:

The present invention provides a pharmaceutical composition for treating hepatitis B virus infection, comprising the crystal entecavir as active ingredients and pharmaceutically acceptable excipients.

The pharmaceutical composition comprises an amount of from 0.001 mg to 25 mg of the crystal entecavir, preferably from 0.01 mg to 10 mg, more preferably from 0.01 mg to 5 mg.

According to the present invention, the pharmaceutically acceptable excipients comprise diluents in an amount of from 50% to 90% by weight of the total composition, and the diluents adheres with the crystal entecavir by an adhesive.

The diluents include one or more compounds selected from lactose, starch, microcrystalline cellulose, sucrose, glucose, mannitol, xylitol, maltitol, dextrin, calcium sulfate and calcium phosphate, in which lactose, starch and microcrystalline cellulose are preferred.

According to the present invention, the adhesives include one or more compounds selected from povidone, hydroxypropylmethylcellulose, alginic acid, sodium alginate, carbomer, poloxamer, and gelatin, in which povidone is preferred. The adhesive is present in an amount of from 2% to 18% by weight of the total composition.

According to the present invention, the pharmaceutical composition further comprises glidants and disintegrants.

Said glidants include one or more compounds selected from silica, stearic acid, magnesium stearate, sodium stearate, calcium stearate, sodium lauryl sulfate, sucrose fatty acid ester, and talcum powder, in which silica and magnesium stearate are preferred. Said glidant is present in an amount of from 0.1% to 5% by weight of the total composition.

Said disintegrants include one or more compounds selected from sodium carboxymethyl starch, hydroxypropyl cellulose, croscarmellose sodium, crospovidone, and sodium starch glycolate, in which sodium carboxymethyl starch is preferred. Said disintegrant is present in an amount of from 1% to 5% by weight of the total composition.

In addition, the pharmaceutical composition is formulated in the form for administration by any suitable means. Preferably, the pharmaceutical composition is formulated in the form of tablets and capsules.

Tablets and capsules of crystal entecavir can respectively be produced by directly tabletting or filling, and then the tablets are further coated so as to have outer film coating. The coating may be sugar coating or film coating, and the film coating is preferred. Suitable materials for use in the film coating are coating agents, light-screening agents, pigments, plasticizers, solubilizing agents, etc. The coating agents include hydroxypropylmethyl cellulose, hydroxyethyl cellulose, hydroxypropyl cellulose, hydroxypropyl methylcellulose phthalate, hypromellose phthalate etc., and hydroxypropyl methyl cellulose is preferred. The light-screening agents include titanium dioxide. The pigments include various iron oxides. The plasticizers include polyethylene glycol. Solubilizing agents include polysorbate 80. The above coating ingredients are dispersed in a suitable solvent, preferably water. The coating ingredients can be applied to the tables using conventional pan coating techniques.

In addition, the present invention also provides a method of preparing for the pharmaceutical composition, which comprises the following steps:

(1) sieving the crystal entecavir as a pharmaceutically active ingredient and the glidant through 120 mesh screen and mixing them together to obtain a mixture;

(2) uniformly mixing the mixture of Step (1) with the diluent, adhesive and disintegrant, and then compressing it into tablets or filling into capsules.

In addition, the present invention further provides uses of the pharmaceutical composition in preparing for pharmaceuticals of treating hepatitis B virus infection.

It has been found from experiments that the tablet and capsule of the pharmaceutical composition produced by the crystal entecavir in an aqueous solution as active ingredients have more stronger stabilization than that of amorphous entecavir under conditions of lighting, high temperature and high humidity.

DETAILED DESCRIPTION AND PREFERRED EMBODIMENTS THEREOF

Hereafter, the crystal entecavir formulations of the present invention will be described specifically with reference to examples. The examples are given only for illustration of the technical solution of the present invention and should not be construed to limit the present invention.

As stated above, the crystal entecavir used as active ingredients of the present invention is that disclosed by the present inventors in Chinese patent application No. 200710004988.9 (corresponding to US Patent Publication No. 2010/0210669, U.S. application Ser. No. 12/527,215, which is a national phase application of PCT/CN2008/000249, the contents of which are incorporated herein in their entirety by reference). The crystalline entecavir has the X-ray powder crystal diffraction pattern (XRD), thermogravimetry-differential scanning calorimetry pattern (TG-DSC) and Fourier transform infrared spectrogram (IR) illustrated in FIGS. 1-3, respectively. The X-ray powder crystal diffraction pattern using a copper target has stronger diffraction peaks at 2θ of 5.3±0.2°, 15.6±0.2°, and 21.2±0.2°. The crystalline form of entecavir is a desolvation product or a product containing water of crystallization. The product containing water of crystallization is the crystalline form of entecavir containing one water of crystallization.

To prepare the crystalline entecavir used in the formulations described herein, a crude product of entecavir is dissolved with stirring in a polar solvent at the temperature of 50° C.-90° C. in the ratio of the crude product of entecavir to the polar solvent of 1:20-60 (mass). The above solution is slowly cooled to a temperature below 50° C., and a flaky crystal is separated out. After filtering, the crystal is dried under vacuum at the temperature of 50° C. to give a crystalline form of entecavir. It has been found by the inventors that the above method is easy to operate and has a good repeatability.

Figure 1:
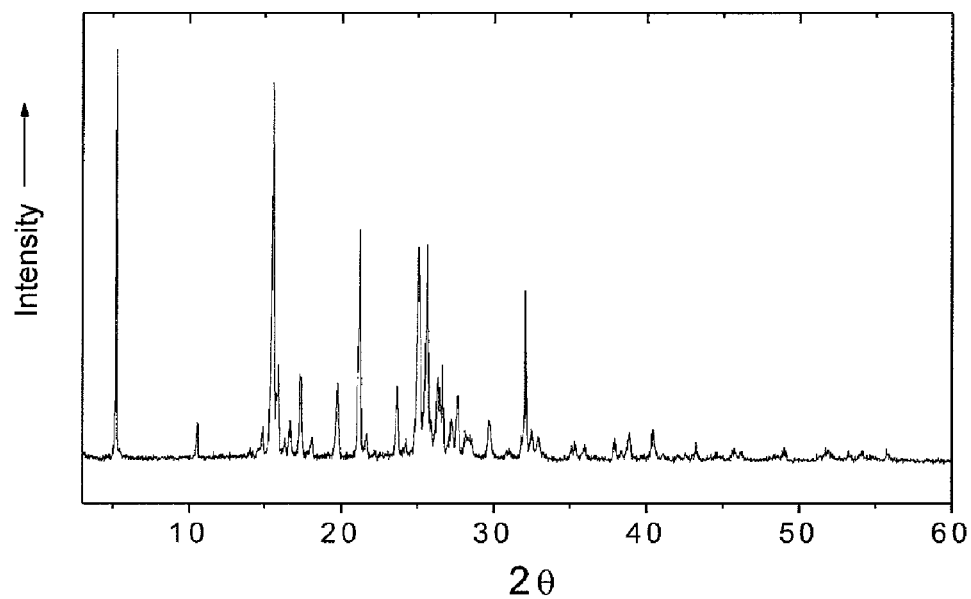
FIG. 1 is a X-ray powder crystal diffraction pattern of a crystalline form of entecavir.

To characterize the crystalline entecavir by XRD, a sample of the crystalline entecavir prepared as described above is characterized by using a Bruker D8 Advance X-ray powder crystal diffraction instrument, and the range of diffraction 2θ angle of 3° to 60°, a scanning step width of 0.02°, a rate of 0.2 s per step, and a X-ray wavelength λ of 0.15406 nm. The X-ray powder crystal diffraction pattern of the above crystalline entecavir is shown in FIG. 1, which shows strong diffraction peaks at 2θ=5.282° (d=16.7171 Å), 2θ=15.560° (d=5.6902 Å), and 2θ=21.236° (d=4.1803 Å). Table 1 provides the data of the major diffraction peaks of the crystalline entecavir of FIG. 1 in which 2θ is the diffraction angle, d is the interplanar spacing of the crystal, and I is the relative intensity of the diffraction peak.

TABLE 1

| 2θ (°) | d (Å) | I % |
|---|---|---|
| 5.282 | 16.7171 | 100.0 |
| 10.573 | 8.3601 | 8.6 |
| 14.876 | 5.9501 | 6.0 |
| 15.560 | 5.6902 | 89.7 |
| 15.895 | 5.5710 | 21.4 |
| 16.643 | 5.3223 | 7.3 |
| 17.304 | 5.1205 | 19.5 |
| 19.741 | 4.4935 | 18.1 |
| 21.236 | 4.1803 | 55.5 |
| 21.658 | 4.0999 | 6.1 |
| 23.681 | 3.7540 | 16.3 |
| 25.040 | 3.5533 | 49.5 |
| 25.619 | 3.4743 | 48.8 |
| 25.844 | 3.4445 | 7.6 |
| 26.338 | 3.3810 | 16.7 |
| 26.637 | 3.3438 | 20.6 |
| 27.201 | 3.2757 | 7.9 |
| 27.655 | 3.2229 | 13.5 |
| 28.143 | 3.1682 | 5.5 |
| 28.440 | 3.1358 | 4.6 |
| 29.686 | 3.0069 | 9.2 |
| 32.085 | 2.7874 | 40.0 |
| 32.466 | 2.7555 | 6.8 |
| 32.939 | 2.7170 | 5.5 |
| 38.862 | 2.3155 | 6.3 |
| 40.443 | 2.2285 | 7.1 |

Figure 2:
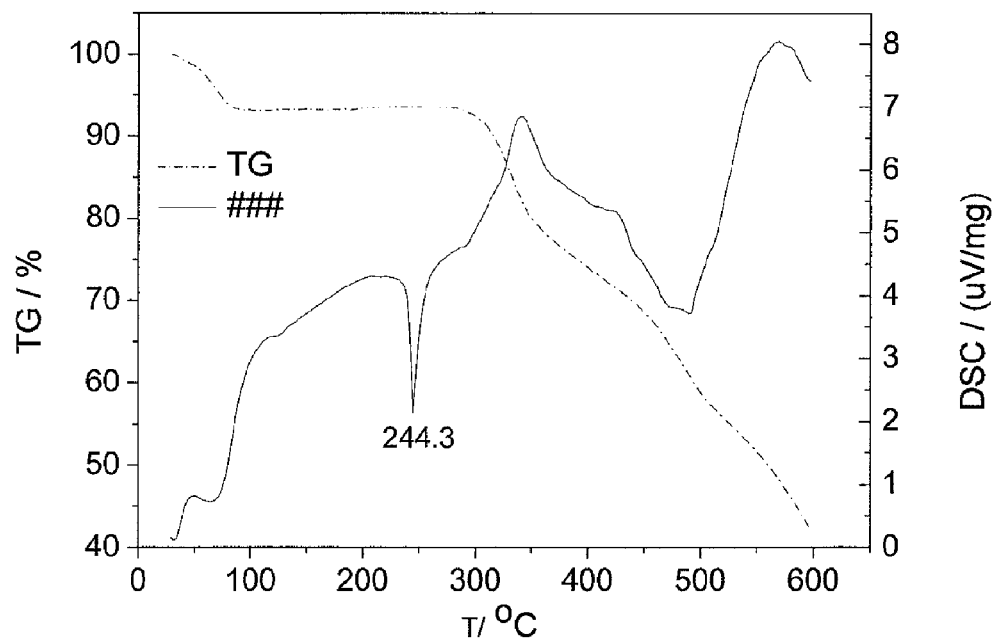
FIG. 2 is thermogravimetry-differential scanning calorimetry pattern of the crystalline form of entecavir.

Thermogravimetry-Differential Scanning Calorimetry (TG-DSC) analysis of the crystalline entecavir under $N_2$ atmosphere was measured by using NETZSCH STA 409 PG/PC type TG-DSC instrument. The heating rate of the sample was 20 K/min. FIG. 2 shows that the weight loss of the sample is about 6% at a temperature of 80° C., which indicates that the sample is a complex of entecavir and a crystalline water of 1:1. The attached FIG. 2 shows a sharp-pointed endothermic peak at the temperature of 244° C. without any weight loss. FIG. 2 illustrates that the melting point of the sample is about 244° C. under the experimental conditions, and the sample will be decomposed when reaching the temperature of 300° C.

Figure 3:
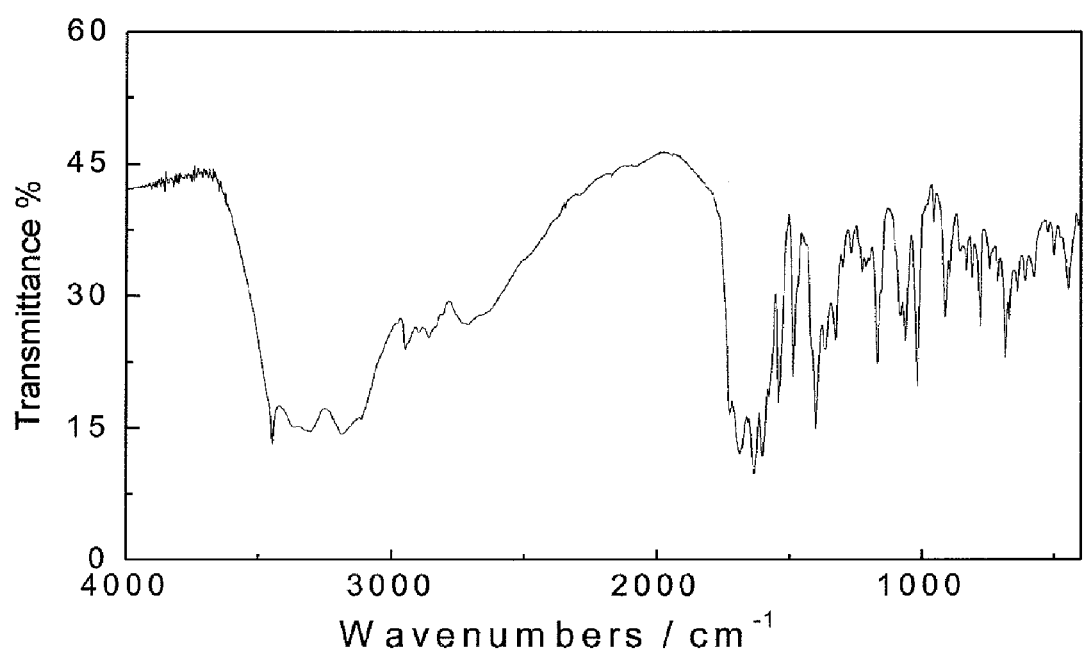
FIG. 3 is Fourier transform infrared spectrogram of the crystalline form of entecavir.

Fourier transform infrared (FTIR) spectrogram: The range of wave numbers is measured by using the Nicolet NEXUS 670 FT-IR spectrometer with KBr pellet method, and the range of wave numbers is about 400 to 4000 $cm^{-1}$. FIG. 3 is a Fourier transform infrared spectrogram of the sample. The infrared spectrogram shows that there are groups in the molecular structure of the sample, such as NH, $NH_2$, HN—C=O, C=C, OH.

Transmission electron microscope: A few solid samples were dispersed in ethanol under the ultrasonic wave. Then the sample was placed on a copper screen coating a carbon membrane, and after the evaporating of ethanol, the shape and particle size of the crystalline form of entecavir was observed by using a JEM-200 CX transmission electron microscope. The accelerating voltage of the transmission electron microscope was about 160 kV. It was seen that the sample was a small, flaky crystal, hexagon in shape with 1 to 5 micron in a particle size.

Solubility: At a room temperature, the crystalline form of entecavir is insoluble in water, slightly soluble in ethanol, sparingly soluble in N,N-dimethylformamide, and soluble in dimethyl sulfoxide.

In a second general aspect of the invention, preparation of tablets of the crystalline form of entecavir may be carried by the following procedure: The crystalline entecavir disclosed herein, microcrystalline cellulose, lactose, carboxymethyl starch sodium and magnesium stearate are respectively screened by 100 mesh size to reserve. The crystalline entecavir, microcrystalline cellulose and lactose are weighed, thoroughly mixed, and a starch paste is added to form a soft material. Damp particles are screened by 14 mesh size. The damp particles are dried for 2 hours at about the temperature of 70° C. to give dry particles, and then screened by 14 mesh size to get dry particles. Then carboxymethyl starch sodium and magnesium stearate are added to the dry particles. After mixing thoroughly, the mixture is prepared to be depressed. The above samples are taken to measure a moisture content of the particles, and the weight of the tablet and its control range are calculated. Then core tablets are obtained by using a 7.0 mm hollow circle mold. A coating powder is prepared and then is added to purified water under stirring to prepare a homogenous suspension containing 20% solid content to reserve. After removed fine powders and small flashes around the edge, the core tablets are put into a coating pan and heated to the temperature of 45° C.-55° C., and then a coating solution is sprayed into the coating pan and dried in hot air at a temperature of 50° C. to 60° C. The spouting velocity, air temperature at the inlet, and air temperature at the outlet are adjusted until the surface of the core tablets are wet but not adherent. After the core tablets are coated to a suitable coating, the liquid spraying is stopped and the tablets are dried by hot air. Then the film coating tablets are taken out of the coating apparatus to obtain tablets of crystalline entecavir. The weight increment of the coating is controlled to about 4%.

TABLE 2

| | Names of Raw and Supplemental Materials | Amount (g) |
|---|---|---|
| Tablet Cores | Crystalline forms of entecavir, | 0.5 |
| | Microcrystalline cellulose | 95.0 |
| | Lactose | 45.3 |
| | Starch paste | 5.0 (calculated according to starch) |
| | Carboxymethyl starch sodium | 3.0 |
| | Magnesium stearate | 1.2 |
| Film Coating | Hypromellose | 3.6 |
| | Titanium dioxide | 0.78 |
| | Talcum powder | 0.78 |
| | Polyethylene glycol | 0.84 |
| | Purified water | 24.0 |
| Making into | 1000 tablets | |

Examples according to the first aspect of the invention are provided below:

Example 1

| Ingredients: | |
|---|---|
| Crystal entecavir | 0.001 g |
| Stearic acid | 1.999 g |
| Sucrose | 50 g |
| Calcium sulfate | 40 g |
| Poloxamer | 3 g |
| Hydroxypropyl cellulose | 5 g |

1000 tablets (weight: 100 mg per tablet) are produced.

Preparation method is as follows:

The crystal entecavir and stearic acid are respectively sieved through 120 mesh screen and uniformly mixed to obtain a mixture, then the mixture is uniformly mixed with sucrose, calcium sulfate, poloxamer and hydroxypropyl cellulose, and then compressed into a tablet.

Example 2

| Ingredients: | |
| --- | --- |
| Crystal entecavir | 0.01 g |
| Silica | 0.05 g |
| Magnesium stearate | 0.05 g |
| Lactose | 89.89 g |
| Povidone | 5 g |
| Sodium carboxymethyl starch | 5 g |

1000 tablets (weight: 100 mg per tablet) are produced.

The crystal entecavir, silica and magnesium stearate are respectively sieved through 120 mesh screen and uniformly mixed to obtain a mixture, then the mixture is uniformly mixed with lactose, povidone and sodium carboxymethyl starch, and then compressed into a tablet.

Example 3

| Ingredients: | |
| --- | --- |
| Crystal entecavir | 0.1 g |
| Sucrose fatty acid ester | 5 g |
| Starch | 81.9 g |
| Alginic acid | 8 g |
| Hydroxypropyl cellulose | 2 g |
| Sodium starch glycolate | 3 g |

1000 tablets (weight: 100 mg per tablet) are produced.

Preparation method is as follows:

The crystal entecavir and sucrose fatty acid ester are respectively sieved through 120 mesh screen and uniformly mixed to obtain a mixture, then the mixture is uniformly mixed with starch, alginic acid, hydroxypropyl cellucose and sodium starch glycolate, and then compressed into a tablet.

Example 4

| Ingredients: | |
| --- | --- |
| Crystal entecavir | 0.5 g |
| Sodium stearate | 3 g |
| Lactose | 45 g |
| Starch | 38.5 g |
| Hydroxypropylmethyl cellulose | 10 g |
| Crospovidone | 3 g |

1000 tablets (weight: 100 mg per tablet) are produced.

Preparation method is as follows:

The crystal entecavir and sodium stearate are respectively sieved through 120 mesh screen and uniformly mixed to obtain a mixture, then the mixture is uniformly mixed with lactose, starch, hydroxypropylmethyl cellulose and crospovidone, and then compressed into a tablet.

Example 5

| Ingredients: | |
| --- | --- |
| Crystal entecavir | 0.5 g |
| Silica | 1.5 g |
| Magnesium stearate | 1.5 g |
| Lactose | 25 g |
| Starch | 30 g |
| Microcrystalline cellulose | 34.5 g |
| Povidone | 6 g |
| Sodium carboxymethyl starch | 3 g |

1000 tablets (weight: 100 mg per tablet) are produced.

Preparation method is as follows:

The crystal entecavir, magnesium stearate and silica are respectively sieved through 120 mesh screen and uniformly mixed to obtain a mixture, then the mixture is uniformly mixed with lactose, starch, microcrystalline cellulose, povidone and sodium carboxymethyl starch, and then compressed into a tablet.

Example 6

| Ingredients: | |
| --- | --- |
| Crystal entecavir | 1 g |
| Silica | 1.5 g |
| Magnesium stearate | 1.5 g |
| Starch | 84 g |
| Povidone | 10 g |
| Sodium carboxymethyl starch | 2 g |

1000 tablets (weight: 100 mg per tablet) are produced.

Preparation method is as follows:

The crystal entecavir, silica and magnesium stearate are respectively sieved through 120 mesh screen and uniformly mixed to obtain a mixture, then the mixture is uniformly mixed with starch, povidone and sodium carboxymethyl starch, and then compressed into a tablet.

Example 7

| Ingredients: | |
| --- | --- |
| Crystal entecavir | 1.5 g |
| Sodium lauryl sulfate | 5 g |
| Microcrystalline cellulose | 87.5 g |
| Carbomer | 4 g |
| Croscarmellose sodium | 2 g |

1000 tablets (weight: 100 mg per tablet) are produced.

Preparation method is as follows:

The crystal entecavir and sodium lauryl sulfate are respectively sieved through 120 mesh screen and uniformly mixed to obtain a mixture, then the mixture is uniformly mixed with microcrystalline cellulose, carbomer and croscarmellose sodium, and then compressed into a tablet.

Example 8

| Ingredients: | |
|---|---|
| Crystal entecavir | 2 g |
| Magnesium stearate | 3 g |
| Lactose | 38 g |
| Microcrystalline cellulose | 50 g |
| Povidone | 2 g |
| Sodium carboxymethyl starch | 5 g |

1000 tablets (weight: 100 mg per tablet) are produced.

Preparation method is as follows:

The crystal entecavir and magnesium stearate are respectively sieved through 120 mesh screen and uniformly mixed to obtain a mixture, then the mixture is uniformly mixed with lactose, microcrystalline cellulose, povidone and sodium carboxymethyl starch, and then compressed into a tablet.

Example 9

| Ingredients: | |
|---|---|
| Crystal entecavir | 5 g |
| Silica | 5 g |
| Microcrystalline cellulose | 71 g |
| Povidone | 18 g |
| Sodium carboxymethyl starch | 1 g |

1000 tablets (weight: 100 mg per tablet) are produced.

Preparation method is as follows:

The crystal entecavir and silica are respectively sieved through 120 mesh screen and uniformly mixed to obtain a mixture, then the mixture is uniformly mixed with microcrystalline cellulose, povidone and sodium carboxymethyl starch, and then compressed into a tablet.

Example 10

| Ingredients: | |
|---|---|
| Crystal entecavir | 10 g |
| Sodium stearate | 2 g |
| Talcum powder | 2 g |
| Glucose | 30 g |
| Calcium phosphate | 40 g |
| Hydroxypropylmethyl cellulose | 11 g |
| Sodium starch glycolate | 5 g |

1000 tablets (weight: 100 mg per tablet) are produced.

Preparation method is as follows:

The crystal entecavir, sodium stearate and talcum powder are respectively sieved through 120 mesh screen and uniformly mixed to obtain a mixture, then the mixture is uniformly mixed with glucose, calcium phosphate, hydroxypropylmethyl cellulose and sodium starch glycolate, and then filled into a No. 4 size of capsule.

Example 11

| Ingredients: | |
|---|---|
| Crystal entecavir | 15 g |
| Stearic acid | 4 g |
| Xylitol | 43 g |
| Maltitol | 30 g |
| Gelatin | 6 g |
| Croscarmellose sodium | 2 g |

1000 tablets (weight: 100 mg per tablet) are produced.

Preparation method is as follows:

The crystal entecavir and stearic acid are respectively sieved through 120 mesh screen and uniformly mixed to obtain a mixture, then the mixture is uniformly mixed with xylitol, maltitol, gelatin and croscarmellose sodium, and then filled into a No. 4 size of capsule.

Example 12

| Ingredients: | |
|---|---|
| Crystal entecavir | 25 g |
| Sodium lauryl sulfate | 2.5 g |
| Sucrose fatty acid ester | 2.5 g |
| Mannitol | 30 g |
| Dextrin | 20 g |
| Alginic acid | 6 g |
| Sodium alginate | 9 g |
| Cropovidone | 5 g |

1000 tablets (weight: 100 mg per tablet) are produced.

Preparation method is as follows:

The crystal entecavir, sodium lauryl sulfate and sucrose fatty acid ester are respectively sieved through 120 mesh screen and uniformly mixed to obtain a mixture, then the mixture is uniformly mixed with mannitol, dextrin, alginic acid, sodium alginate and crospovidone, and then filled into a No. 4 size of capsule.

Comparative Example 1

| Ingredients: | |
|---|---|
| Amorphous entecavir | 0.001 g |
| Stearic acid | 1.999 g |
| Sucrose | 50 g |
| Calcium sulfate | 40 g |
| Poloxamer | 3 g |
| Hydroxypropyl cellulose | 5 g |

1000 tablets (weight: 100 mg per tablet) are produced.

Preparation method is as follows:

The amorphous entecavir and stearic acid are respectively sieved through 120 mesh screen and uniformly mixed to obtain a mixture, then the mixture is uniformly mixed with sucrose, calcium sulfate, poloxamer and hydroxypropyl cellulose, and then compressed into a tablet.

Comparative Example 2

| Ingredients: | |
| --- | --- |
| Amorphous entecavir | 0.01 g |
| Silica | 0.05 g |
| Magnesium stearate | 0.05 g |
| Lactose | 89.89 g |
| Povidone | 5 g |
| Sodium carboxymethyl starch | 5 g |

1000 tablets (weight: 100 mg per tablet) are produced.

Preparation method is as follows:

The amorphous entecavir, silica and magnesium stearate are respectively sieved through 120 mesh screen and uniformly mixed to obtain a mixture, then the mixture is uniformly mixed with lactose, povidone and sodium carboxymethyl starch, and then compressed into a tablet.

Comparative Example 3

| Ingredients: | |
| --- | --- |
| Amorphous entecavir | 0.1 g |
| Sucrose fatty acid ester | 5 g |
| Starch | 81.9 g |
| Alginic acid | 8 g |
| Hydroxypropyl cellulose | 2 g |
| Sodium starch glycolate | 3 g |

1000 tablets (weight: 100 mg per tablet) are produced.

Preparation method is as follows:

The amorphous entecavir and sucrose fatty acid ester are respectively sieved through 120 mesh screen and uniformly mixed to obtain a mixture, then the mixture is uniformly mixed with starch, alginic acid, hydroxypropyl cellucose and sodium starch glycolate, and then compressed into a tablet.

Comparative Example 4

| Ingredients: | |
| --- | --- |
| Amorphous entecavir | 0.5 g |
| Sodium stearate | 3 g |
| Lactose | 45 g |
| Starch | 38.5 g |
| Hydroxypropylmethyl cellulose | 10 g |
| Crospovidone | 3 g |

1000 tablets (weight: 100 mg per tablet) are produced.

Preparation method is as follows:

The amorphous entecavir and sodium stearate are respectively sieved through 120 mesh screen and uniformly mixed to obtain a mixture, then the mixture is uniformly mixed with lactose, starch, hydroxypropylmethyl cellulose and crospovidone, and then compressed into a tablet.

Comparative Example 5

| Ingredients: | |
| --- | --- |
| Amorphous entecavir | 0.5 g |
| Silica | 1.5 g |
| Magnesium stearate | 1.5 g |
| Lactose | 25 g |
| Starch | 30 g |
| Microcrystalline cellulose | 34.5 g |
| Povidone | 6 g |
| Sodium carboxymethyl starch | 3 g |

1000 tablets (weight: 100 mg per tablet) are produced.

Preparation method is as follows:

The amorphous entecavir, magnesium stearate and silica are respectively sieved through 120 mesh screen and uniformly mixed to obtain a mixture, then the mixture is uniformly mixed with lactose, starch, microcrystalline cellulose, povidone and sodium carboxymethyl starch, and then compressed into a tablet.

Comparative Example 6

| Ingredients: | |
| --- | --- |
| Amorphous entecavir | 1 g |
| Silica | 1.5 g |
| Magnesium stearate | 1.5 g |
| Starch | 84 g |
| Povidone | 10 g |
| Sodium carboxymethyl starch | 2 g |

1000 tablets (weight: 100 mg per tablet) are produced.

Preparation method is as follows:

The amorphous entecavir, silica and magnesium stearate are respectively sieved through 120 mesh screen and uniformly mixed to obtain a mixture, then the mixture is uniformly mixed with starch, povidone and sodium carboxymethyl starch, and then compressed into a tablet.

Comparative Example 7

| Ingredients: | |
| --- | --- |
| Amorphous entecavir | 1.5 g |
| Sodium lauryl sulfate | 5 g |
| Microcrystalline cellulose | 87.5 g |
| Carbomer | 4 g |
| Croscarmellose sodium | 2 g |

1000 tablets (weight: 100 mg per tablet) are produced.

Preparation method is as follows:

The amorphous entecavir and sodium lauryl sulfate are respectively sieved through 120 mesh screen and uniformly mixed to obtain a mixture, then the mixture is uniformly mixed with microcrystalline cellulose, carbomer and croscarmellose sodium, and then compressed into a tablet.

Comparative Example 8

| Ingredients: | |
| --- | --- |
| Amorphous entecavir | 2 g |
| Magnesium stearate | 3 g |
| Lactose | 38 g |
| Microcrystalline cellulose | 50 g |
| Povidone | 2 g |
| Sodium carboxymethyl starch | 5 g |

1000 tablets (weight: 100 mg per tablet) are produced.

Preparation method is as follows:

The amorphous entecavir and magnesium stearate are respectively sieved through 120 mesh screen and uniformly mixed to obtain a mixture, then the mixture is uniformly mixed with lactose, microcrystalline cellulose, povidone and sodium carboxymethyl starch, and then compressed into a tablet.

Comparative Example 9

| Ingredients: | |
| --- | --- |
| Amorphous entecavir | 5 g |
| Silica | 5 g |
| Microcrystalline cellulose | 71 g |
| Povidone | 18 g |
| Sodium carboxymethyl starch | 1 g |

1000 tablets (weight: 100 mg per tablet) are produced.

Preparation method is as follows:

The amorphous entecavir and silica are respectively sieved through 120 mesh screen and uniformly mixed to obtain a mixture, then the mixture is uniformly mixed with microcrystalline cellulose, povidone and sodium carboxymethyl starch, and then compressed into a tablet.

Comparative Example 10

| Ingredients: | |
| --- | --- |
| Amorphous entecavir | 10 g |
| Sodium stearate | 2 g |
| Talcum powder | 2 g |
| Glucose | 30 g |
| Calcium phosphate | 40 g |
| Hydroxypropylmethyl cellulose | 11 g |
| Sodium starch glycolate | 5 g |

1000 tablets (weight: 100 mg per tablet) are produced.

Preparation method is as follows:

The amorphous entecavir, sodium stearate and talcum powder are respectively sieved through 120 mesh screen and uniformly mixed to obtain a mixture, then the mixture is uniformly mixed with glucose, calcium phosphate, hydroxypropylmethyl cellulose and sodium starch glycolate, and then filled into a No. 4 size of capsule.

Comparative Example 11

| Ingredients: | |
| --- | --- |
| Amorphous entecavir | 15 g |
| Stearic acid | 4 g |
| Xylitol | 43 g |
| Maltitol | 30 g |
| Gelatin | 6 g |
| Croscarmellose sodium | 2 g |

1000 tablets (weight: 100 mg per tablet) are produced.

Preparation method is as follows:

The amorphous entecavir and stearic acid are respectively sieved through 120 mesh screen and uniformly mixed to obtain a mixture, then the mixture is uniformly mixed with xylitol, maltitol, gelatin and croscarmellose sodium, and then filled into a No. 4 size of capsule.

Comparative Example 12

| Ingredients: | |
| --- | --- |
| Amorphous entecavir | 25 g |
| Sodium lauryl sulfate | 2.5 g |
| Sucrose fatty acid ester | 2.5 g |
| Mannitol | 30 g |
| Dextrin | 20 g |
| Alginic acid | 6 g |
| Sodium alginate | 9 g |
| Cropovidone | 5 g |

1000 tablets (weight: 100 mg per tablet) are produced.

Preparation method is as follows:

The amorphous entecavir, sodium lauryl sulfate and sucrose fatty acid ester are respectively sieved through 120 mesh screen and uniformly mixed to obtain a mixture, then the mixture is uniformly mixed with mannitol, dextrin, alginic acid, sodium alginate and crospovidone, and then filled into a No. 4 size of capsule.

Example 13

Eighteen tablets of Examples 1-9 and Comparative examples 1-9 are film coated with commercially film coating powder by using conventional Film Coating Techniques.

| Ingredients of the coating solution is as follows: | |
| --- | --- |
| Opadry ®II | 2 mg~5 mg |
| Pure water | appropriate |

Note: The pure water used in coating process can be removed by drying. Opadry®II is commercially film coated premixed powders and contains hydroxypropylmethylcellulose, titanium dioxide, polyethylene glycol, and polysorbate 80, as well as various of color starch according to different standards of the series products. The amount of the coating powder used in the formulation is an average amount range of the coating powder per tablet in an account of 100 mg per tablet.

Example 14

| Ingredients: | |
|---|---|
| Crystal entecavir | 5 g |
| Lactose | 72 g |
| Hydroxypropylmethyl cellulose | 17 g |
| Total | 94 g |

Preparation method is as follows:

The crystal entecavir, lactose and hydroxypropylmethyl cellulose are respectively sieved through 120 mesh screen and uniformly mixed to obtain a premixed composition comprising crystal entecavir, lactose and hydroxypropylmethyl cellulose.

After these samples produced by the Examples and the Comparative Examples above are respectively stored for 10 days under the conditions of 60° C. of temperature, 92.5% of Relative Humidity (RH) and 4500 lx±500 lx of illuminance, the amount of each ingredient in each sample is determined by HPLC (area normalized method). Octadecylsilane bonded silica is used as filler, water-acetonitrile-trifluoroacetic acid (990:10:1) is used as a mobile phase A, and water-acetonitrile-trifluoroacetic acid (700:300:1) is used as a mobile phase B. The flow rate is about 1.0 ml/min, the detecting wavelength is about 254 nm, and the temperature of the column is about 30° C. The results are in Table 3 below:

TABLE 3

Stability of the Examples and the Comparative Examples

| | Related substance (%) | | | |
|---|---|---|---|---|
| | 0 day | 60° C. for 10 days | 92.5% RH for 10 days | 4500 lx ± 500 lx for 10 days |
| Example | | | | |
| Example 1 | 0.51 | 1.78 | 0.66 | 1.32 |
| Example 2 | 0.49 | 1.80 | 0.61 | 1.35 |
| Example 3 | 0.51 | 1.68 | 0.58 | 1.44 |
| Example 4 | 0.54 | 1.82 | 0.64 | 1.36 |
| Example 5 | 0.50 | 1.85 | 0.67 | 1.34 |
| Example 6 | 0.47 | 1.90 | 0.60 | 1.41 |
| Example 7 | 0.57 | 1.65 | 0.68 | 1.30 |
| Example 8 | 0.40 | 1.56 | 0.54 | 1.33 |
| Example 9 | 0.43 | 1.77 | 0.57 | 1.34 |
| Example 10 | 0.58 | 1.68 | 0.71 | 1.29 |
| Example 11 | 0.60 | 1.92 | 0.73 | 1.26 |
| Example 12 | 0.52 | 1.84 | 0.63 | 1.28 |
| Comparative Example | | | | |
| Comparative Example 1 | 0.52 | 2.69 | 1.45 | 2.50 |
| Comparative Example 2 | 0.53 | 2.88 | 1.42 | 2.53 |
| Comparative Example 3 | 0.55 | 2.74 | 1.38 | 2.60 |
| Comparative Example 4 | 0.58 | 2.85 | 1.48 | 2.55 |
| Comparative Example 5 | 0.54 | 2.71 | 1.45 | 2.53 |
| Comparative Example 6 | 0.51 | 2.92 | 1.41 | 2.59 |
| Comparative Example 7 | 0.62 | 2.45 | 1.54 | 2.51 |
| Comparative Example 8 | 0.53 | 2.43 | 1.36 | 2.56 |
| Comparative Example 9 | 0.48 | 2.80 | 1.44 | 2.58 |
| Comparative Example 10 | 0.62 | 2.75 | 1.58 | 2.47 |
| Comparative Example 11 | 0.65 | 2.96 | 1.60 | 2.45 |
| Comparative Example 12 | 0.63 | 2.90 | 1.42 | 2.50 |

Note: the related substance is referred to as "impurity", its data shows stability of the products. The amount of the related substance in the product for 0 day is a datum quantity of the related substance. After processes of high temperature, high humidity and lighting, the amount of the related substance may vary, and the more amounts of the related substance increases, the poorer stability of the product is under the condition, vice versa.

It can be shown from the Table 1 that the amount of the related substance of the sample by using the crystal entecavir of the Examples do not remarkably differ from that of using the amorphous entecavir of the Comparative Examples after storing for 0 day. However, after processes of 60° C. of high temperature, 92.5% of high Relative Humidity (RH) and 4500 lx±500 lx of illuminance, the increased amount of the related substance of the sample in the Comparative Examples is obviously larger than that of the Examples. It shows that the stability of the samples by using crystal entecavir of Examples is superior to that of samples by using amorphous entecavir of the Comparative Examples.

The pharmaceutical compositions disclosed herein may consist essentially of one or more of diluents, adhesives, glidants and disintegrants. The pharmaceutical compositions disclosed herein may consist of one or more of diluents, adhesives, glidants and disintegrants. The process of making the pharmaceutical compositions disclosed herein may consist essentially of (1) sieving crystalline entecavir as the sole pharmaceutically active ingredient and a glidant through 120 mesh screen and uniformly mixing them to obtain a mixture; and (2) uniformly mixing the mixture of step (1) with a diluent, adhesive and disintegrant, and then compressing the mixture into tablets or filling into capsules, whereby the resulting tablets or capsules have improved stability, as disclosed herein, relative to tablets or capsules formed with amorphous entecavir. The process of making the pharmaceutical compositions disclosed herein may consist of (1) sieving crystalline entecavir as the sole pharmaceutically active ingredient and a glidant through 120 mesh screen and uniformly mixing them to obtain a mixture; and (2) uniformly mixing the mixture of step (1) with a diluent, adhesive and disintegrant, and then compressing the mixture into tablets or filling into capsules. The tablets may optionally be film coated according to the processes herein.

Although the present invention has been described in connection with the above embodiments, it should be understood that the present invention is not limited to such preferred embodiments and procedures set forth above. The embodiments and procedures were chosen and described in order to best explain the principles of the invention and its practical application, to thereby enable others skilled in the art to best utilize the invention. It will be apparent to those skilled in the art that various substitution, modifications and changes may be thereto without departing from the scope and spirit of the invention. Therefore, the intention is intended to cover all alternative constructions and equivalents falling within the spirit and scope of the invention as defined only by the appended claims and equivalents thereto.

The invention claimed is:

1. A pharmaceutical composition for treating hepatitis B virus infection, comprising the crystal entecavir as the active ingredient and one or more pharmaceutically acceptable excipients, wherein:
   the crystal entecavir has the x-ray diffraction pattern of FIG. 1 and is present at an amount of from 0.001 mg to 25 mg; and the one or more pharmaceutically acceptable excipients comprise one or more of diluents, adhesives, glidants and disintegrants, wherein the diluents comprise one or more compounds selected from lactose, starch, sucrose, glucose, mannitol, xylitol, maltitol, dextrin, calcium sulfate and calcium phosphate, wherein the diluent is present at an amount of from 50% to 90% by weight of the total composition;

the adhesives comprise one or more compounds selected from hydroxypropylmethylcellulose, alginic acid, sodium alginate, carbomer, poloxamer, and gelatin, wherein the adhesive is present in an amount of from 2% to 18% by weight of the total composition;

the glidants comprise one or more compounds selected from silica, stearic acid, sodium stearate, calcium stearate, sodium lauryl sulfate, sucrose fatty acid ester, and talcum powder, wherein the glidant is present in an amount of from 0.1% to 5% by weight of the total composition; and the disintegrants comprising one or more compounds selected from hydroxypropyl cellulose, croscarmellose sodium, and crospovidone, the disintegrant is present in an amount of from 1% to 5% by weight of the total composition.

2. The pharmaceutical composition according to claim 1 wherein the crystal entecavir has an x-ray diffraction pattern of:

| 2θ (°) | d (Å) | I % |
|---|---|---|
| 5.282 | 16.7171 | 100.0 |
| 10.573 | 8.3601 | 8.6 |
| 14.876 | 5.9501 | 6.0 |
| 15.560 | 5.6902 | 89.7 |
| 15.895 | 5.5710 | 21.4 |
| 16.643 | 5.3223 | 7.3 |
| 17.304 | 5.1205 | 19.5 |
| 19.741 | 4.4935 | 18.1 |
| 21.236 | 4.1803 | 55.5 |
| 21.658 | 4.0999 | 6.1 |
| 23.681 | 3.7540 | 16.3 |
| 25.040 | 3.5533 | 49.5 |
| 25.619 | 3.4743 | 48.8 |
| 25.844 | 3.4445 | 7.6 |
| 26.338 | 3.3810 | 16.7 |
| 26.637 | 3.3438 | 20.6 |
| 27.201 | 3.2757 | 7.9 |
| 27.655 | 3.2229 | 13.5 |
| 28.143 | 3.1682 | 5.5 |
| 28.440 | 3.1358 | 4.6 |
| 29.686 | 3.0069 | 9.2 |
| 32.085 | 2.7874 | 40.0 |
| 32.466 | 2.7555 | 6.8 |
| 32.939 | 2.7170 | 5.5 |
| 38.862 | 2.3155 | 6.3 |
| 40.443 | 2.2285 | 7.1. |

3. The pharmaceutical composition according to claim 1, wherein said crystal entecavir is present at an amount of from 0.01 mg to 10 mg.

4. The pharmaceutical composition according to claim 3, wherein said crystal entecavir is present at an amount of from 0.01 mg to 5 mg.

5. The pharmaceutical composition according to claim 1, wherein said pharmaceutical composition is in the form of one or more of tablets and capsules.

6. The pharmaceutical composition according to claim 1, wherein said pharmaceutical composition has an outer film coating.

7. A method of preparing for the pharmaceutical composition according to claim 1, which comprises the following steps:

(1) sieving the crystal entecavir as a pharmaceutically active ingredient and glidant through 120 mesh screen and uniformly mixing them to obtain a mixture;

(2) uniformly mixing the mixture of step (1) with the diluent, adhesive and disintegrant, and then compressing the mixture into tablets or filling into capsules.

8. A method of treating hepatitis B virus infection, the method comprising administrating the pharmaceutical composition of claim 1.

9. A pharmaceutical composition of crystal entecavir as the active ingredient and one or more pharmaceutically acceptable excipients, wherein:

the crystal entecavir has an x-ray diffraction pattern of:

| 2θ (°) | d (Å) | I % |
|---|---|---|
| 5.282 | 16.7171 | 100.0 |
| 10.573 | 8.3601 | 8.6 |
| 14.876 | 5.9501 | 6.0 |
| 15.560 | 5.6902 | 89.7 |
| 15.895 | 5.5710 | 21.4 |
| 16.643 | 5.3223 | 7.3 |
| 17.304 | 5.1205 | 19.5 |
| 19.741 | 4.4935 | 18.1 |
| 21.236 | 4.1803 | 55.5 |
| 21.658 | 4.0999 | 6.1 |
| 23.681 | 3.7540 | 16.3 |
| 25.040 | 3.5533 | 49.5 |
| 25.619 | 3.4743 | 48.8 |
| 25.844 | 3.4445 | 7.6 |
| 26.338 | 3.3810 | 16.7 |
| 26.637 | 3.3438 | 20.6 |
| 27.201 | 3.2757 | 7.9 |
| 27.655 | 3.2229 | 13.5 |
| 28.143 | 3.1682 | 5.5 |
| 28.440 | 3.1358 | 4.6 |
| 29.686 | 3.0069 | 9.2 |
| 32.085 | 2.7874 | 40.0 |
| 32.466 | 2.7555 | 6.8 |
| 32.939 | 2.7170 | 5.5 |
| 38.862 | 2.3155 | 6.3 |
| 40.443 | 2.2285 | 7.1 | the one or more pharmaceutically acceptable excipients comprise one or more of diluents, adhesives, glidants and disintegrants, wherein the diluents comprise one or more compounds selected from lactose, starch, sucrose, glucose, mannitol, xylitol, maltitol, dextrin, calcium sulfate and calcium phosphate, wherein the diluent is present at an amount of from 50% to 90% by weight of the total composition;

the adhesives comprise one or more compounds selected from hydroxypropylmethylcellulose, alginic acid, sodium alginate, carbomer, poloxamer, and gelatin, wherein the adhesive is present in an amount of from 2% to 18% by weight of the total composition;

the glidants comprise one or more compounds selected from silica, stearic acid, sodium stearate, calcium stearate, sodium lauryl sulfate, sucrose fatty acid ester, and talcum powder, wherein the glidant is present in an amount of from 0.1% to 5% by weight of the total composition; and the disintegrants comprising one or more compounds selected from hydroxypropyl cellulose, croscarmellose sodium, and crospovidone, the disintegrant is present in an amount of from 1% to 5% by weight of the total composition, wherein the pharmaceutical composition is prepared in a process comprising:

(1) sieving the crystal entecavir as a pharmaceutically active ingredient and glidant through 120 mesh screen and uniformly mixing them to obtain a mixture; and (2) uniformly mixing the mixture of step (1) with the diluent, adhesive and disintegrant, and then compressing the mixture into tablets or filling into capsules.

10. The pharmaceutical composition of crystal entecavir of claim 9, wherein the pharmaceutical composition is prepared in a process consisting essentially of:
  (1) sieving the crystal entecavir as a pharmaceutically active ingredient and glidant through 120 mesh screen and uniformly mixing them to obtain a mixture; and
  (2) uniformly mixing the mixture of step (1) with the diluent, adhesive and disintegrant, and then compressing the mixture into tablets or filling into capsules.

11. The pharmaceutical composition of claim 10, further comprising film coating the tablets.

12. The pharmaceutical composition of crystal entecavir of claim 9, wherein the pharmaceutical composition is prepared in a process consisting of:
  (1) sieving the crystal entecavir as a pharmaceutically active ingredient and glidant through 120 mesh screen and uniformly mixing them to obtain a mixture; and
  (2) uniformly mixing the mixture of step (1) with the diluent, adhesive and disintegrant, and then compressing the mixture into tablets or filling into capsules.

13. The pharmaceutical composition of claim 12, further comprising film coating the tablets.

14. The pharmaceutical composition of crystal entecavir of claim 9, wherein the entecavir is present in an amount of 0.001 mg to 25 mg per tablet or capsule.

15. A pharmaceutical composition of crystal entecavir as the active ingredient and one or more pharmaceutically acceptable excipients, wherein:
  the crystal entecavir is characterized by strong diffraction peaks at $2\theta=5.282°$ ($d=16.7171$ Å), $2\theta=15.560°$ ($d=5.6902$ Å), and $2\theta=21.236°$ ($d=4.1803$ Å); and
  the one or more pharmaceutically acceptable excipients comprise one or more of diluents, adhesives, glidants and disintegrants, wherein
  the diluents comprise one or more compounds selected from lactose, starch, sucrose, glucose, mannitol, xylitol, maltitol, dextrin, calcium sulfate and calcium phosphate and the diluent is present in an amount of from 50% to 90% by weight of the total composition;
  the adhesives comprise one or more compounds selected from hydroxypropylmethylcellulose, alginic acid, sodium alginate, carbomer, poloxamer, and gelatin and the adhesive is present in an amount of from 2% to 18% by weight of the total composition;
  the glidants comprise one or more compounds selected from silica, stearic acid, sodium stearate, calcium stearate, sodium lauryl sulfate, sucrose fatty acid ester, and talcum powder and the glidant is present in an amount of from 0.1% to 5% by weight of the total composition; and
  the disintegrants comprise one or more compounds selected from hydroxypropyl cellulose, croscarmellose sodium, and crospovidone and the disintegrant is present in an amount of from 1% to 5% by weight of the total composition.

16. The pharmaceutical composition of claim 15, wherein the crystal entecavir has an x-ray diffraction pattern of:

| $2\theta$ (°) | d (Å) | I % |
| --- | --- | --- |
| 5.282 | 16.7171 | 100.0 |
| 10.573 | 8.3601 | 8.6 |
| 14.876 | 5.9501 | 6.0 |
| 15.560 | 5.6902 | 89.7 |
| 15.895 | 5.5710 | 21.4 |
| 16.643 | 5.3223 | 7.3 |
| 17.304 | 5.1205 | 19.5 |
| 19.741 | 4.4935 | 18.1 |
| 21.236 | 4.1803 | 55.5 |
| 21.658 | 4.0999 | 6.1 |
| 23.681 | 3.7540 | 16.3 |
| 25.040 | 3.5533 | 49.5 |
| 25.619 | 3.4743 | 48.8 |
| 25.844 | 3.4445 | 7.6 |
| 26.338 | 3.3810 | 16.7 |
| 26.637 | 3.3438 | 20.6 |
| 27.201 | 3.2757 | 7.9 |
| 27.655 | 3.2229 | 13.5 |
| 28.143 | 3.1682 | 5.5 |
| 28.440 | 3.1358 | 4.6 |
| 29.686 | 3.0069 | 9.2 |
| 32.085 | 2.7874 | 40.0 |
| 32.466 | 2.7555 | 6.8 |
| 32.939 | 2.7170 | 5.5 |
| 38.862 | 2.3155 | 6.3 |
| 40.443 | 2.2285 | 7.1. |

\* \* \* \* \*